(12) United States Patent
Moser et al.

(10) Patent No.: US 7,732,599 B2
(45) Date of Patent: Jun. 8, 2010

(54) PROCESS FOR PREPARING TETRAHYDROBIOPTERIN AND ANALOGS OF TETRAHYDROBIOPTERIN

(75) Inventors: Rudolf Moser, Schaffhausen (CH); Viola Groehn, Dachsen (CH); Andreas Schumacher, Efringen-Kirchen (DE); Pierre Martin, Rheinfelden (CH); Dirk Spielvogel, Freiburg (DE)

(73) Assignees: BioMarin Pharmaceutical Inc., Novato, CA (US); Merck Eprova AG, Schaffhausen (CH)

( * ) Notice: Subject to any disclaimer, the term of this patent is extended or adjusted under 35 U.S.C. 154(b) by 688 days.

(21) Appl. No.: 10/579,106

(22) PCT Filed: Nov. 17, 2004

(86) PCT No.: PCT/US2004/038313

§ 371 (c)(1),
(2), (4) Date: Feb. 16, 2007

(87) PCT Pub. No.: WO2005/049614

PCT Pub. Date: Jun. 2, 2005

(65) Prior Publication Data

US 2007/0244322 A1 Oct. 18, 2007

Related U.S. Application Data

(60) Provisional application No. 60/520,367, filed on Nov. 17, 2003, provisional application No. 60/520,368, filed on Nov. 17, 2003.

(51) Int. Cl.
*C07D 487/00* (2006.01)
*C07D 491/00* (2006.01)

(52) U.S. Cl. .................................................. 544/251
(58) Field of Classification Search .................. 544/251
See application file for complete search history.

(56) References Cited

FOREIGN PATENT DOCUMENTS

| EP | 0165595 | 12/1985 |
|---|---|---|
| JP | 1221380 | * 9/1989 |

OTHER PUBLICATIONS

Aizpurua et al., "Reaction of Hindered Trialkylsilyl Esters and Trialkylsilyl Ethers with Triphenylphosphine Dibromide: Preparation of Carboxylic Acid Bromides and Alkyl Bromides under Mild Neutral Conditions", *J. Org. Chem.*, 51(25):4941-4943 (1986).

Ashton et al., "Amino Acid Derivatives of β-Cyclodextrin", *J. Org. Chem.*, 61(3):903-908 (1996).

Bell et al., "The Reduction of Organic Halogen Compounds by Sodium Borohydride", *J. Org. Chem.*, 34:3923-3926 (1969).

Blau et al., "Disorders of Tetrahydrobiopterin and Related Biogenic Amines," *The Metabolic and Molecular Bases of Inherited Disease, 8th Ed.*, Chapter 78, pp. 1725-1776 (2001).

Bradshaw et al., "Synthesis of the Organic Ligand of the Molybdenum cofactor, in protected form", *J. Chem. Soc.*, 1:3239-3244 (2001).

Bredereck et al., "Darstellung und Eigenschaften der Amidacetale und Aminalester", *Chem. Ber.*, 101:41-50 (1968).

Chaudhary et al., "4-Dimethylaminopyridine: An Efficient and Selective Catalyst for the Silylation of Alcohols", *Tet. Let.*, 2:99-102 (1979).

Corey et al., "Protection of Hydroxyl Groups as tert-Butyldimethylsilyl Derivatives", *J. Am. Chem. Soc.*, 94(17):6190-6191 (1972).

Green et al., "Protective Groups in Organic Synthesis," *Wiley & Sons, 3rd Ed.*, pp. 201-245 (1999).

Hanaya et al., "Selective N(3)-and $O^4$-Alkylation of L-Biopterin: A Convenient Synthesis of 3-and $O^4$-Methyl-L-biopterin and the Versatile $N^2$-(N,N-dimethylaminomethylene)-N(3)-p-nitrophenethyl-Protected L-Biopterin", *Pteridines*, 6(1):1-7 (1995).

Hanessian et al., "Reactions of Carbohydrates with (Halomethylene)dimethyliminium Halides and Related Reagents. Synthesis of Some Chlorodeoxy Sugars", *J. Org. Chem.*, 34(7):2163-2170 (1969).

Hart et al., *J. Organic. Chem.*, vol. 68, No. 1, pp. 187-190 (2003).

Hutchins et al., "Sodium Borohydride in Dimethyl Sulfoxide or Sulfolane. Convenient Systems for Selective Reductions of Primary, Secondary and Certain Tertiary Halides and Tosylates", *Tet. Let.*, No. 40, pp. 3495-3498 (1969).

International Search Report, International Application No. PCT/US2004/038313, dated Jan. 11, 2007.

Kaiser et al., "80. Synthesis of Biopterin from Neopterin? The Formation of Pyrrolo[1,2-*f*]pteridins upon Side-Chain Activation of Neopterin", *Helv. Chim. Acta.*, 70:766-770 (1987).

(Continued)

*Primary Examiner*—James O Wilson
*Assistant Examiner*—Erich A Leeser
(74) *Attorney, Agent, or Firm*—Jones Day

(57) ABSTRACT

Process for the preparation of tetrahydrobiopterin from neopterin and/or 6-substituted pterins with an improved yield and a high stereoselectivity. Also disclosed herein are novel individual intermediates prepared in the preparation of tetrahydrobiopterin, such as selectively protected neopterin useful for the preparation of tetrahydrobiopterin.

7 Claims, 4 Drawing Sheets

OTHER PUBLICATIONS

Kim et al., "Direct Conversion of Silyl Ethers into Alkyl Bromides with Boron Tribromide", *J. Org. Chem.*, 53:3111-3113 (1988).

Kang et al., "Synthesis of 2-ethylthio-6-(3-hydroxy-1,2-O-Isopropylidenepropyl)pteridin-4(3H)-One", *Heterocycles*, 53(7):1551-1557 (2000).

Kikuchi et al., "Synthesis of (-)-Biopterin Using (S)-Ethyl Lactate as a Starting Material", *Agric. Biol. Chem.*, 53(8):2095-2100 (1989).

Larock, "8. Electrophilic Acylation. 1. Synthesis of Aldehydes", *Comprehensive Organic Transformations, Wiley VCH, 2nd Ed.*, pp. 681-708 (1999).

Mattes et al., "Reactivity of t-butyldimethylsilyl ethers: a facile conversion into bromides", *Tet. Let.*, 28(15):1697-1698 (1987).

Patterson et al., "The Synthesis of a Pteridine Required for the Growth of *Crithidia fasciculata.*", *J. Am. Chem. Soc.*, vol. 78:5868-5871 (1956).

Pellicciari et al., "Stereospecific Synthesis of the Enantiomers of Nicotinylalanine, a Neuroprotecting Agent", *Tet, Let.*, 33:3003-3004 (1992).

Ross et al., "Anodic Oxidations. V. The Kolbe Oxidation of Phenylacetic Acid and 1-Methylcyclohexaneacetic Acid at Platinum and at Carbon", *The Journal of Organic Chemistry*, 24:2923-2927 (1969).

Russell et al., "Model Studies Related to the Cofactor of the Oxomolybdoenzymes; Part 6: An Improved Synthesis of 6-Substituted Pterins from 2,4,5-Triamino-6-hydroxy-pyrimidine and D-Glucose", *Synlett*, pp. 711-712 (1992).

Russell et al., "Model Studies Related to the Cofactor of the Oxomolybdoenzymes. Part 5. Synthesis of 6-Alkenyl- and 6-Alkynylpterins", *Tet. Let.*, 33(23):3371-3374 (1992).

Schircks et al., "Eine neue, regiospezifische Synthese von L-Biopterin", *Helv. Chim. Acta.*, 60:211-214 (1977).

Smith et al., "March's Advanced Organic Chemistry, Reactions Mechanisms and Structure," Wiley & Sons, Inc., 5th Ed., pp. 524-526 (2001).

Soyka et al., "Synthese und Eigenschaften von 5,6-Dihydro-6-(1,2,3-trihydroxypropyl)pteridinen: Kovalente intromolekulare Addukte", *Helv. Chim. Acta.*, 73:808-826 (1990).

Sugimoto et al., "The Convenient Syntheses of Biopterin and Its Three Opitical Isomers", *Bull. Chem. Soc. Jpn.*, 48:3767-3768 (1975).

Taylor et al., "An Unequivocal Total Synthesis of L-erythro-Biopterin", *J. Am. Chem. Soc.*, 96:6781-6782 (1974).

Viscontini et al., "Synthese des natürlichen D-neopterins und L-Monapterins", *Helv. Chim. Acta.*, 53:1202-1207 (1970).

Viscontini et al., "Eine neue Synthese von D, L-Biopterin", *Helv. Chim. Acta.*, 55:574-579 (1972).

Written Opinion of the International Searching Authority, International application No. PCT/US2004/038313, dated Jan. 11, 2007.

Zinner et al., "Die partielle Veresterung von D-Arabinose-mercaptalen mit Sulfonsaurechloriden und eine einfache Synthese der 5-Desoxy-D-arabinose", *Chem. Ber.*, 92:1618-1623 (1959).

Zinner et al., "Synthese and Derivate der 2.5-Didesoxy-D-ribose", *Chem. Ber.*, 92:2893-2896 (1959).

\* cited by examiner

PROCESS FOR PREPARING TETRAHYDROBIOPTERIN AND ANALOGS OF TETRAHYDROBIOPTERIN

CROSS-REFERENCE TO RELATED APPLICATION

This application claims the benefit under 35 U.S.C. §119 (e) of U.S. Provisional Patent Applications Ser. Nos. 60/520,367 and 60/520,368, both filed Nov. 17, 2003, the disclosures of which are hereby incorporated herein by reference.

BACKGROUND

1. Field of the Technology

The invention relates to a method for preparing tetrahydrobiopterin and related compounds and analogs of biopterin. More specifically, it relates to a stereoselective process for preparing 5,6,7,8-tetrahydro-6-(L-erythro-1',2'-dihydroxypropyl)pterin and includes the conversion of 6-(L-erythro-1,2,3-trihydroxypropyl)pterin and/or 6-substituted pterins to tetrahydrobiopterin.

2. Brief Description of Related Technology

Tetrahydrobiopterin is a biogenic amine of the naturally-occurring pterin family. Pterins are present in physiological fluids and tissues in reduced and oxidized forms, however, only the 5,6,7,8-tetrahydrobiopterin is biologically active. Tetrahydrobiopterin is a chiral molecule, and the 6R enantiomer, and 1'R,2'S,6R diastereomer of the tetrahydrobiopterin is the known biologically active form. The synthesis and disorders of tetrahydrobiopterin are described in Blau et al., Disorders of tetrahydrobiopterin and related biogenic amines, in Scriver C R, Beaudet A L, Sly W S, Valle D, Childs B, Vogelstein B, eds. The Metabolic and Molecular Bases of Inherited Disease, 8th ed., New York: McGraw-Hill, 2001, at pages 1275-1776.

In a living body tetrahydrobiopterin plays a very important role as cofactor of essential enzymes (e.g., the aromatic amino acid hydroxylases, the nitric oxide synthetases, as a coenzyme in a catecholamine-serotonin synthesis.) Tetrahydrobiopterin is an indispensable compound for biosynthesis of the neurotransmitters dopamine and hydroxytyptamine, of noradrenalin, adrenaline, and melatonin. The importance of tetrahydrobiopterin has been recognized in the course of the fundamental studies thereon. A deficiency of tetrahydrobiopterin causes serious neurological disorders like phenylketonuria (PKU) and Parkinson's disease. Symptoms due to such diseases can be remarkably improved by administration of tetrahydrobiopterin. Further, it has been recognized that tetrahydrobiopterin is effective for curing infantile autism and depressions.

Such useful pharmacological activities, as well as the challenging chemical structures of the molecule, have stimulated many synthetic efforts directed toward the preparation of tetrahydrobiopterin. For example, tetrahydrobiopterin has been prepared by: (1) the reaction of 4-hydroxy-2,5,6-triaminopyrimidine (TAP) and 5-deoxy-L-arabinose as described in E. L. Patterson et al., J. Am. Chem. Soc., 78, 5868 (1956); (2) the reaction of TAP and 5-deoxy-L-arabinose phenylhydrazone, as described in Matsuura et al., Bull. Chem. Soc. Jpn., 48, 3767 (1975); (3) the reaction of TAP and triacetyloxy-5-deoxy-L-arabinose phenylhydrazone, as described in M. Viscontini et al., Helv. Chim. Acta., 60, 211 (1977); (4) the reaction of oxime and benzyl α-aminocyanoacetate and condensation of the resulting 3-(1,2-dihydroxypropyl)-pyrazine-1-oxide derivatives with guanidine followed by deoxygenation of the N-oxide, as described in E. C. Taylor et al., J. Am. Chem. Soc., 96, 6781 (1974); (5) the reaction of α-hydroxyketone (prepared from crotonic acid) and TAP, as described in M. Viscontini et al., Helv. Chim. Acta., 55, 574 (1972); and (6) the reaction of TAP having protected hydroxyl group and 4-acetoxy-2,3-epoxypentanal followed by oxidation with iodine and deprotection, as described in Matsuura et al., Chemistry of Organic Synthesis, Vol. 46, No. 6, p. 570 (1988), by protecting the hydroxyl group of S-alkyl lactate with a trityl group, reducing the resulting alkyl 2-trityloxypropionate to (S)-2-trityloxypropanol, oxidizing it to (S)-2-trityloxypropanal, treating it with a 2-furyl metal compound to form (1S,2S)-1-(2-furyl)-2-trityloxy-1-propanal followed by oxidation and hydrolysis to form 2,3-dideoxy-6-trityloxy-hepto-2-enopyranose-4-ulose, reducing it to 6-trityloxy-hepto-2-ene-1,4,5-triol, acylating it to from 1,4,5-triacyloxy-6-trityloxyhepto-2-ene followed by oxidation to afford 2,3 diacyloxy-4-hydroxy-1-pentanal, treating it with phenylhydrazine to from a hydrazine, and condensing the hydrazine with a 3,5,6-triaminopyrimidinol followed by oxidation and deacylation, as described in Japanese Kokai No. 221380/1989.

Each of these conventional processes for preparing tetrahydrobiopterin have several drawbacks, including, for example, expensive and sparsely available carbohydrates are required as starting material to provide the asymmetric carbon atom at its side-chain, in that yield and purity are low due to multi-reaction steps, unstable intermediates are generated that require troublesome treatment operations, and troublesome purification procedures are required.

The prior processes for preparing tetrahydrobiopterin starting from 5-deoxy-L-arabinose are economically disadvantageous, since 5-deoxy-L-arabinose of the required purity is only not readily available in large quantities. Also the product from the reactions involving 5-deoxy-L-arabinose is known to undergo degradation. Other prior preparation of tetrahydrobiopterin have the disadvantage that biopterin is produced in a DL-form and optical resolution is required for obtaining the desired L-biopterin, thus leading to complicated process step and low yield. Indeed, in A. Kaiser, H. P. Wessel, Helv. Chim. Acta, Vol. 70, p. 766, 1987, states at page 768, that "These results and considerations demonstrate that no high-yield synthesis of biopterin from neopterin can be expected due to pyrrolo-pteridin formation upon activation of the side-chain terminus of neopterin."

Therefore, the conventional processes are unsuitable for industrial production of the compound and its derivatives. There exists a need for a process for the preparation of tetrahydrobiopterin, and analogs thereof in good yield using inexpensive starting material. A need also exists for an industrial scale process for the preparation of substantially optically pure tetrahydrobiopterin with an improved yield and a high stereoselectivity.

SUMMARY

One aspect of the processes and compounds described herein is a preparation of tetrahydrobiopterin from neopterin with an improved yield and a high stereoselectivity for the natural type (6R)-form. In one aspect, the method comprises the steps of protecting the 2-amino group of neopterin with a 2-amino protective group, which may make the product more soluble, followed by carrying out a selective reaction on the primary hydroxyl group. In one embodiment, the primary hydroxyl group of neopterin is selectively protected with a primary hydroxyl protecting group, the secondary hydroxyl groups also selectively protected with a secondary hydroxyl protecting group, and reduction is carried out on the primary hydroxyl position in the side chain. In another embodiment, the primary hydroxyl group of neopterin is converted to its corresponding thioether, and reduction is carried out on this thioether. Deprotection of any of these groups may take place at any suitable time; for example, deprotecting the 2-amino group may occur immediately after selective protection of the primary hydroxyl group or may occur later. Alternatively, the method optionally includes erythro-selective reduction The method optionally includes the step of hydrogenating and/or crystallizing tetrahydrobiopterin dihydrochloride.

Another aspect of the processes and compounds described herein is preparation of tetrahydrobiopterin from 6-substituted pterins including the steps of metalation of a protected 6-substituted pterin and coupling with lactic acid or a precursor of lactic acid. The method optionally includes the step of erythro-selective reduction of the 1'-keto group. Deprotection may take place at any suitable time; for example, immediately before erythro-selective reduction or afterwards. The method optionally includes the step of hydrogenating and/or crystallizing tetrahydrobiopterin dihydrochloride.

Yet another aspect of the present invention relates to novel individual intermediates, such as selectively protected pterin derivatives.

Further aspects and advantages of the invention will be apparent to those skilled in the art from a review of the following detailed description, taken in conjunction with the appended claims. While the processes and compounds are susceptible of embodiments in various forms, the description hereinafter includes specific embodiments of the invention with the understanding that the disclosure is illustrative, and is not intended to limit the inventions to the specific embodiments described herein.

DETAILED DESCRIPTION OF THE PREFERRED EMBODIMENTS

Tetrahydrobiopterin is a heterocyclic compound that performs a central role in a number of biological processes. The general structure of tetrahydrobiopterin is shown below:

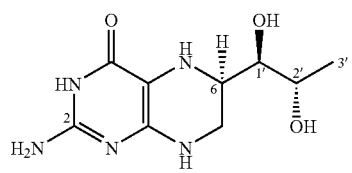

Tetrahydrobiopterin contains three consecutive stereocenters, labeled above as 6, 1', and 2'. Tetrahydrobiopterin, like a number of biologically active molecules, exhibits a substantially heightened biological activity when a single stereoisomer and enantiomer. Described herein are processes for the preparation of a substantially single enantiomer and stereoisomer of tetrahydrobiopterin, and analogs thereof.

The substantially optically pure compound L-Neopterin (CAS No 2277-43-2) is used as the starting material in one embodiment of the processes described herein. The general structure of L-Neopterin is shown below:

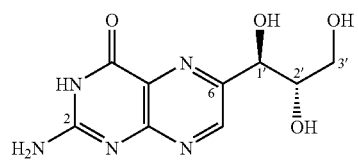

Figure 1:
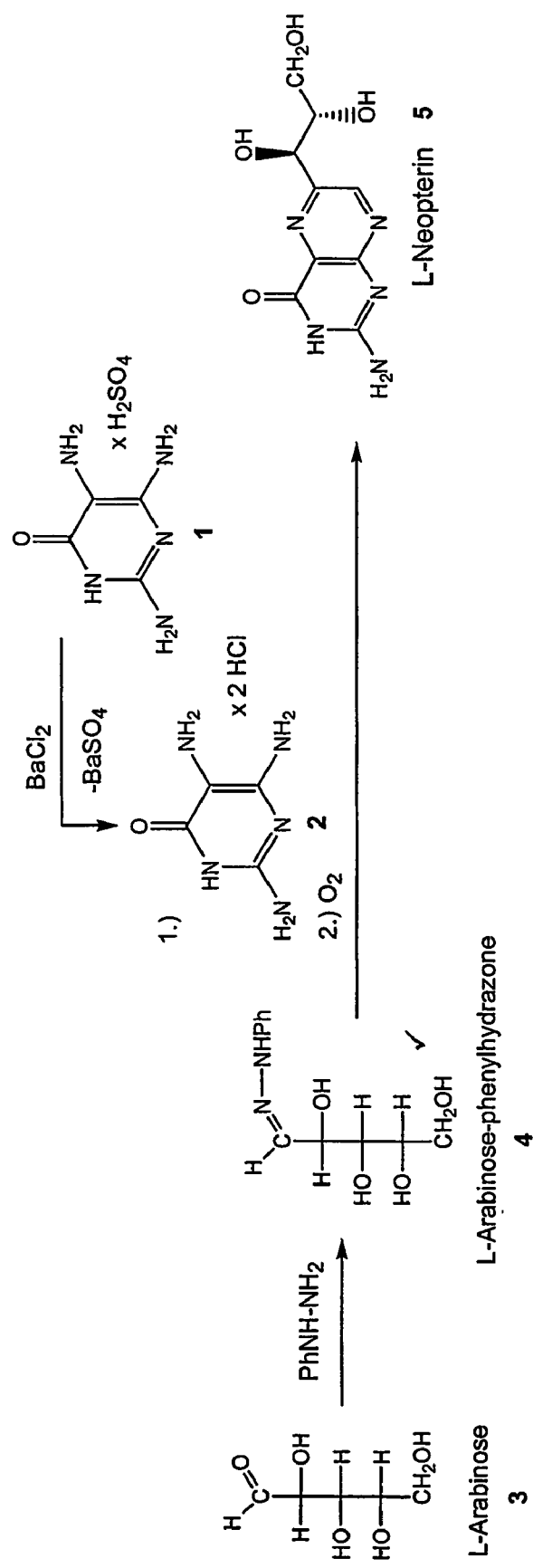
FIG. 1 is a schematic representation of the reaction scheme for preparing L-Neopterin.

A schematic representation of the process for preparing L-Neopterin from L. Arabinose is shown in FIG. 1 (L-Neopterin is also available from Schircks Laboratories of Jona, Switzerland). The process for preparing L-Neopterin is also described in Pfleiderer et al, Helv. Chim. Acta, Vol. 73, p. 808 (1990), and Viscontini et al, Helv. Chim. Acta, Vol. 53, p. 1202 1970, the disclosures of which are hereby incorporated herein by reference.

As used herein, the terms "linear chain alkyl" and "branch chain allyl" encompasses, alkyl groups that may contain as few as one carbon atom or as many as fourteen carbon atoms, including but not limited to, cycloalkyl groups, methyl, ethyl, propyl, isopropyl, t-butyl, sec-butyl, cyclopentyl or cyclohexyl groups. The terms "linear chain alkyl" and "branch chain alkyl" also include alkyl groups that may be substituted with a variety of substituents, including but are not limited to, acyl, aryl, alkoxy, aryloxy, carboxy, hydroxy, carboxamido and/or N-acylamino moieties.

As used herein, an "aryl" encompasses, but is not limited to, a phenyl, pyridyl, pyrryl, indolyl, naphthyl, thiophenyl or furyl group, each of which may be substituted by various groups, which includes, but are not limited, acyl, aryl alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthoxy. Examples of acyloxy groups include, but are not limited to, acetoxy, propanoyloxy, butyryloxy, pentanoyloxy and hexanoyloxy.

As used herein, the terms "alkoxycarbonyl", "acyl" and "alkoxy" encompass, but are not limited to, methoxycarbonyl, ethoxycarbonyl, propoxycarbonyl, n-butoxycarbonyl, benzyloxycarbonyl, hydroxypropylcarbonyl, aminoethoxycarbonyl, secbutoxycarbonyl and cyclopentyloxycarboniyl. Examples of acyl groups include, but are not limited to, formyl, acetyl, propionyl, butyryl and penanoyl. Examples of alkoxy groups include, but are not limited to, methoxy, ethoxy, propoxy, n-butoxy, sec-butoxy and cyclopentyloxy.

The solvent medium useful in the reactions of the processes described herein includes a wide variety of solvents. The reactions described herein are preferably performed wherein the reaction starting materials (e.g., 6-substituted neopterin, neopterin, neopterin derivatives, biopterin and tetrahydrobiopterin) are dissolved in the solvent medium. Thus, the solvents used in the reactions described herein are preferably polar solvents capable of dissolving the polar compounds used and created according to the processes described herein.

Preferably, the solvent is N,N-dimethylformamide (also referred to herein as DMF). Preferably, the concentration of the reactants in the reaction mixture is in the range of about 0.1% to about 20% by weight, more preferably 0.2% to 10%. Though the materials quickly dissolve in a polar reaction medium, at the beginning of a reaction the substances can exist in a solid form. In such a case, the substances can be gradually dissolved in the medium as the reaction proceeds.

One embodiment of the processes and compounds described herein includes a process for forming enantiomerically-enriched tetrahydrobiopterin or a salt thereof from neopterin, including the following steps: (a) reacting the primary hydroxyl group of neopterin with a silyl protecting group; (b) protecting the secondary hydroxyl groups with a secondary hydroxyl-protecting group; (c) converting the silyl group formed in step (b) to a surrogate group selected from the group consisting of halogens, sulfonates, and thioethers; (d) reduction at the substituted formed in step (e) to a methyl group; and (e) removing the secondary hydroxyl-protecting group added at step (d). Step (c) can be performed by: i) direct conversion of the primary hydroxyl protecting group to a halogen; or (ii) selective cleavage of the silylether followed by a conversion of the protected primary hydroxyl group to a group selected from the group consisting of halogens, sulfonates, and thioethers. Preferably, the conversion in step (e) is performed by a direct conversion of the primary hydroxyl protecting group to a halogen. It has been found that this embodiment of the processes described herein can be performed without the protection of the 2-amino group on the neopterin. Under certain circumstances (e.g., in order to avoid side reactions and degradation) it may be preferable to first protect the 2-amino group of L-Neopterin before performing step (a) as described above. If the process of this embodiment is performed with the use of a 2-amino protecting group, the 2-amino protecting group is preferably removed after step (a) is performed. An example of the reactions of this process, wherein the 2-amino groups are protected/deprotected, is exemplified in FIG. 2.

Figure 2:
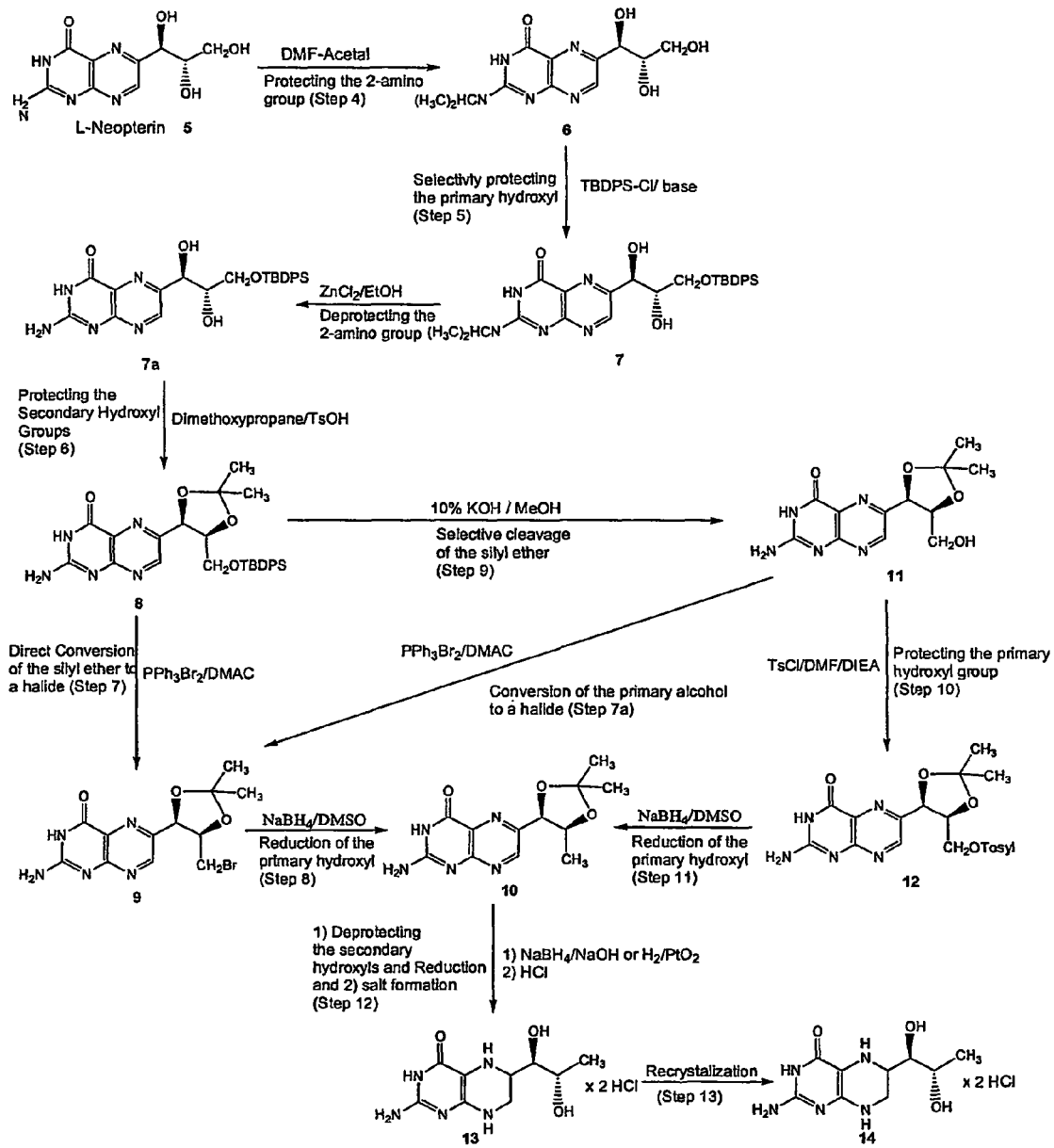
FIG. 2 is a schematic representation of a process described herein for the conversion of L-Neopterin to Tetrahydrobiopterin dihydrochloride salt.

As exemplified in FIG. 2 as Step 4, the 2-amino group can be protected before performing step (a). The protection of the 2-amino group on the L-Neopterin is preferably performing using a variety of protecting groups. Preferably, the protecting group for the 2-amino position on L-Neopterin is selected from the group consisting of dialkylformamidedialkylacetal groups, and pivaloyl groups. More preferably, the protecting group is one of N,N-dimethylformamidediethylacetal, and N,N-dimethylformamidedimethylacetal.

Protecting the 2-amino group dialkylformamidedialkylacetals yields the selective protection of the 2-amino group, and is described in Brederick et al, Chem. Ber., 101 41-50, (1968), and generally in Russel et al., Synlett 1992, p. 711, the disclosures of which are hereby incorporated herein by reference. Preferably, the reaction to protect the 2-amino group is carried out in a polar solvent, more preferably in dimethylformamide. In addition the 2-(N,N-dialkylaminomethylene-imino) Neopterin derivatives are much more soluble in non-polar organic solvents than the unprotected neopterin, and the protection of the 2-amino group to with a 2-(N,N-dialkylaminomethylene-imino) protecting group could be performed in a less polar solvent than DMF.

Another embodiment of the processes and compounds described herein is a compound of Formula 6, which is prepared according to Step 4:

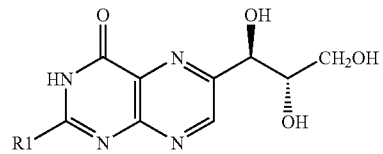

wherein R1 is selected from the group consisting of single substituted linear chain alkyl groups, single substituted branched chain alkyl groups, aryl substituted amido groups, an acetamido group, and a 2,2-dimethylpropanamido group. Preferably, R1 preferably single linear chain alkyl substituted alkylaminomethylene-imine groups, single branched chain alkyl substituted alkylaminomethylene-imine groups, double linear chain alkyl substituted alkylaminomethylene-imine groups, and double branched chain alkyl substituted alkylaminomethylene-imine groups.

Another protecting group that can be used to protect the 2-amino group is an acyl group, preferably a pivaloyl group. These compounds are obtained by the preparation of the acyl or tetrapivaloylderivative of neopterin, followed by an alkaline hydrolysis of the three ester groups, as described in the literature, e.g., Russell et al., Tet. Let., vol. 33, No. 23, pp 3371-3374 (1992), the disclosure of which is hereby incorporated herein by reference.

Another embodiment of the processes and compounds described herein is a 2-amino protected derivative of L-Neopterin of Formula 15:

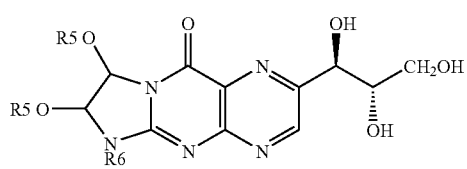

wherein R5 is —COR', R' is selected from the group consisting of linear chain alkyl groups, branched chain alkyl groups, aryl groups, and t-butyl; and R6 is selected from the group consisting of linear chain alkyl groups, branched chain alkyl groups, and aryl groups.

The next step in the process, as exemplified in FIG. 2 as Step 5, is the selective protection of the primary hydroxyl group of a compound of Formula 6 (as prepared according to Step 4), to yield a compound of Formulae 7 and 7a (both shown below).

Another embodiment of the processes and compounds described herein is a compound of Formula 7 (prepared according to Step 5):

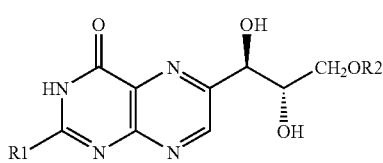

wherein R1 is selected from the group consisting of single linear chain alkyl substituted amino groups, single branched chain alkyl substituted amino groups, double linear chain alkyl substituted amino groups, aryl single substituted amino groups, linear chain alkyl substituted sulfur groups, branched chain alkyl substituted sulfur groups, and 2,2-dimethylpropanamide; and wherein R2 is a silyl group that is stable under acidic conditions. Preferably, R1 comprises N,N-dimethylaminomethylene amino, and R2 is selected from the group consisting of diethylisopropylsilyl, dimethylisopropylsilyl, dimethylphenylsilyl, diphenylisopropoxysilyl, diphenyl-t-butoxysilyl, di-t-butylmethylsilyl, di-t-butylsilylene, methyldiisopropylsilyl, methyldiphenylsilyl, t-butylmethoxyphenylsilyl, t-butyldimethylsilyl, thexyldimethylsilyl, triethylsilyl, 1,1,3,3,-tetra-isopropyldisiloxane, triisopropylsilyl, trimethylsilyl, trimethylsilyloxycabomyl, and t-butyldiphenylsilanoyl. More preferably, R2 is t-butyldiphenylsilanoyl.

Other protecting groups and details of processes for their introduction/removal may be found by reference to Hart et al, J. Organic. Chem., 68(1) (2003), Corey et al, J. Am. Chem. Soc., 94(17) (1972), or Chaudary et al, Tet. Let., 2, pp 99-102 (1979), the disclosures of which are hereby incorporated herein by reference. The selective protection reaction is preferable carried out in a polar solvent, more preferably in dimethylformamide. The use of alkylchlorosilanes reagents as protecting agents yields in a highly selective protection of the primary hydroxyl function. According to this method there was no observed influence on the secondary hydroxyl groups within the molecule. The reaction is carried out in presence of a base, preferably the base is imidazole. The selective protection step can also be carried with a compound of Formula 15.

When a 2-amino protecting group is utilized in this embodiment, is possible to selectively cleave of the protection group at the 2-amino function with an in situ reaction. When the 2-amino group is protected as an acyl group, the selective deprotection can be performed with ammonium hydroxide in dioxane, when the 2-amino group is protected as a linear or branched chain alkyl substituted sulfur group, the selective deprotection can be performed with ammonium hydroxide, when the 2-amino group is protected as an N,N-dimethylaminomethylene substituted amino group, the selective deprotection can be performed with ammonium hydroxide in dioxane and preferably with zinc dichloride in ethanol. The selective deprotection of the 2-amino group yields Formula 7a.

Thus, another embodiment of the processes and compounds described herein is a compound of Formula 7a:

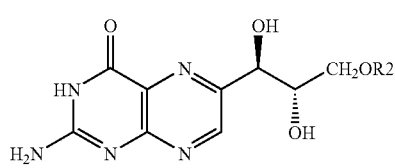

7a wherein R2 is a silyl group that is stable under acidic conditions. Preferably, R2 is selected from the group consisting of diethylisopropylsilyl, dimethylisopropylsilyl, dimethylphenylsilyl, diphenylisopropoxysilyl, diphenyl-t-butoxysilyl, di-t-butylmethylsilyl, di-t-butylsilylene, methyldiisopropylsilyl, methyldiphenylsilyl, t-butylmethoxyphenylsilyl, t-butyldimethylsilyl, thexyldimethylsilyl, triethylsilyl, 1,1,3,3,-tetra-isopropyldisiloxane, triisopropylsilyl, trimethylsilyl, trimethylsilyloxycabomyl, and t-butyldiphenylsilanoyl. More preferably, R2 is t-butyldiphenylsilane The next step in the process, as exemplified in FIG. 2 as Step 6, is the protection of the secondary hydroxyl groups of a compounds of Formulae 7 and/or 7a (as prepared according to example shown in Step 5), to yield a compound of Formula 8 (shown below).

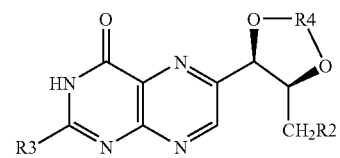

8 wherein R3 is selected from the group consisting of $NH_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; R2 is a silyl group that is stable under acidic conditions; and R4 a substituted acetal or ketal group that is stable under alkaline conditions. Preferably, R4 is a substituted acetal or ketal group is selected from the group consisting of linear alkyl substituted acetals or ketals, branched alkyl chain substituted acetals or ketals, and aryl substituted acetals or ketals. More preferably, R4 is selected from the group consisting of methylene acetal, ethylidene acetal, t-butylmethylidene ketal, 1-t-butylethylidene ketal, 1-phenylethylidene ketal, 1-(4-methoxyphenyl)ethylidene acetal, 2,2,2-trichloroethylidene acetal, acrolein acetal, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, 4-nitrobenzylidene acetal, mesitylene acetal, 1-naphthaldehyde acetal, benzophenone ketal, and isopropylideneketal.

Cyclic ortho-esters and other 1,2-diol protective groups which are stable to alkaline conditions and cleaved under acidic conditions are suitable protecting groups for the secondary hydroxyl groups.

The reaction of exemplified in FIG. 2 as Step 6 is preferably performed a polar solvent, more preferably in acetone. Also preferable, R4 is acetonedimethylacetal, and the reaction is performed in acetone and in the presence of p-toluenesulfonic acid. Other protecting groups and details of processes for their introduction/removal may be found in "Protective Groups in Organic Synthesis", Green et al., 3$^{rd}$ Ed. (1999) Wiley & Sons, p 201-245, the disclosure of which is hereby incorporated herein by reference.

The next step or series of steps in the process, as exemplified in FIG. 2 as Step 7, and Step 9 and Step 7a conversion of the silyl ether to a halide. As shown, for example in FIG. 2, Step 7, the silyl ether (such as in a compound of Formula 8) is directly converted to a halide, and exemplified in Steps 9 and 7a of FIG. 2, the conversion goes through a deprotection step. Through either pathway, the result is the formation of a compound of Formula 9 (shown below).

Thus, another embodiment of the processes and compounds described herein is a compound of Formula 9:

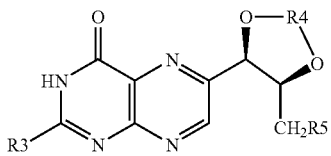

wherein R3 is selected from the group consisting of $NH_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; R4 is selected from the group consisting of linear alkyl substituted acetals or ketals, branched alkyl chain substituted acetals or ketals, and aryl substituted acetals or ketals; and wherein R5 is a halogen.

The halogen is preferably introduced into the molecule by triphenylphosphine halogen, preferably with triphenylphosphine bromide. The reaction is preferably carried out a solvent selected from the group consisting of dichloromethane, dimethylformamide, and dimethylacetamide. Other reaction conditions and details of the conversion of the silyl ether to a halide can be found in Hanessian et al, J. Org. Chem., 34(7), p 2163 (1969), Kim et al, J. Org. Chem., 53, p 3111-3113 (1988), Ashton, J. Org. Chem., 61(3), p905 (1996), Aizpurua et al, J. Org. Chem., 51(25), p 4942 (1986), and Mattes, Tet. Let., 28(15), p 169 (1987), the disclosures of which are hereby incorporated herein by reference.

As described above, an alternative method for the preparation of a compound of Formula 9 includes the deprotection of the primary hydroxyl followed by the formation of the halide. As exemplified in FIG. 2 as Step 9, when a compound of Formula 8 is treated with a base in a protic solvent (e.g., KOH in $CH_3OH$), the silyl ether protecting group is cleaved to form a compound of Formula 11. Thus, another embodiment of the processes and compounds described herein is a compound of Formula 11:

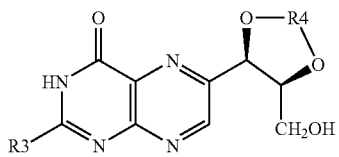

wherein P3 is selected from the group consisting of $NH_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; and R4 is selected from the group consisting of linear alkyl substituted acetals or ketals, branched alkyl chain substituted acetals or ketals, and aryl substituted acetals or ketals.

The deprotection of the primary hydroxyl group as described above (e.g., as exemplified in Step 9 of FIG. 2) is preferably carried out in an alcohol, more preferably in methanol. The conversion may also be achieved by using fluorides (e.g., tetrabutylammoniumfluoride in tetrahydrofuran or other apolar solvents.

The deprotected primary hydroxyl group is then converted to a halide as shown, for example, in Step 7a in FIG. 2. This conversion is performed under the same conditions as described above for example shown in Step 7 of FIG. 2, and yields a compound of Formula 9. Further details regarding the reaction conditions and processes for this conversion can be found in "Comprehensive Organic Transformations", R. C. Larock, 2nd ed., Wiley VCH, p689-697 (1999), the disclosure of which is hereby incorporated herein by reference.

As an alternative to the preparation of a compound of Formula 9, the primary hydroxyl group on a compound of Formula 11 can be converted to a sulfonate group (e.g., a tosylate group) such as in a compound of Formula 12, such as, for example, as shown in Step 10 of FIG. 2. Thus, another embodiment of the processes and compounds described herein is a compound of Formula 12:

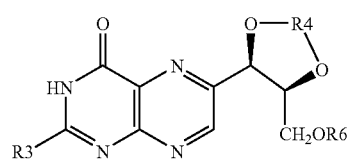

wherein R3 is selected from the group consisting of $NH_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; R4 is selected from the group consisting of linear alkyl substituted acetals or ketals, branched alkyl chain substituted acetals or ketals, and aryl substituted acetals or ketals; and R6 is selected from the group consisting of linear chain alkyl substituted sulfonates, branched chain alkyl substituted sulfonates, and aryl substituted sulfonates. Preferably, R4 is dimethylacetal, R3 is an N,N-dimethylaminomethylene substituted amino group, and R6 is a tosyl group. The reaction exemplified in Step 10 of FIG. 2 is preferably carried out with sulfonylchloride in the presence of a base.

The next step in the process is the preparation of a compound of Formula 10. Both compounds of Formulae 9 and 12 can be converted to a compound of Formula 10. As an example, these conversions are exemplified in FIG. 2 as Step 11, and Step 8. Thus, another embodiment of the processes and compounds described herein is a compound of Formula 10:

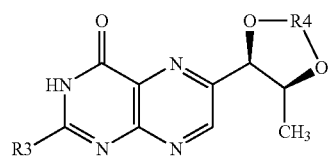

wherein R3 is selected from the group consisting of $NH_2$, 2,2-dimethylpropanamide, single linear chain alkyl substituted amino groups, single branched chain alkyl substituted amino groups, double linear chain alkyl substituted amino groups, double branched chain all substituted amino groups, aryl single substituted amino groups, linear chain alkyl substituted sulfur groups, and branched chain alkyl substituted sulfur groups; and R4 is selected from the group consisting of linear alkyl substituted acetals or ketals, branched alkyl chain substituted acetals or ketals, and aryl substituted acetals or ketals. Preferably, R4 is dimethylacetal, and R3 is an N,N-dimethylaminomethylene substituted amino group.

The reduction of a compound of Formulae 12 and 9 is preferably carried out with sodium borohydride and/or lithium aluminum hydride, and preferably in a polar, non-aqueous aprotic solvent such as dimethyl sulfoxide, dimethylformamide or sulfolane. Other reaction conditions and details of regarding this step can be found in "March's Advanced Organic Chemistry, Reaction Mechanisms and Structures" by Smith and March, 5th edition, Wiley & Sons, Inc., p. 524-526 (2001), European Patent No. 0 165 595 A2, Zinner et al, Chem. Ber., 92, 1618 (1959), Zinner et al, Chem. Ber., 92, 2893 (1959), Bell et al, J. Org. Chem., 34, 3923 (1969), Hutchins et al, Tel. Let., 3495 (1969), and Hutchins et al, J. Org. Chem., 24, 2923, (1969), the disclosures of which are hereby incorporated herein by reference.

As an alternative of the preparation of process a halide of Formula 9 and a tosylate of Formula 12, a sulfonate can be prepared from the deprotected alcohol of Formula 11. As described below, the sulfonate can be converted into its corresponding thioether with the use of the Mitsunobu reaction, and then the resulting thioether can be reduced to yield a compound of Formula 10. Thus, another embodiment of the processes and compounds described herein is a compound of Formula 11a:

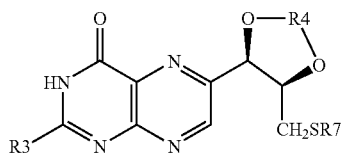

11a wherein R3 is selected from the group consisting of NH$_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; R4 is selected from the group consisting of linear alkyl substituted acetals or ketals, branched alkyl chain substituted acetals or ketals, and aryl substituted acetals or ketals; and R7 is selected from the group consisting of linear chain alkyl groups, branched chain alkyl groups, and aryl groups.

This reaction to convert a compound of Formula 11a into a compound of Formula 10 is preferably performed using the Mitsunobu reaction (e.g., PPh3/ROOCN=NCOOR), followed by reduction of the resulting thioether using, for example, Raney-Nickel. Preferably, the reduction of the thioether is performed using a Raney-Nickel and hydrogen, more preferably Raney-Nickel, hydrogen, in an ethanol solvent medium.

The next step in the process, as exemplified in FIG. 2 as Step 12, is the reduction of a compound of Formula 10 (as prepared according to Steps 8 and 12), to stereoselectively yield tetrahydrobiopterin. The tetrahydrobiopterin can then be converted to its salt form, including but not limited to its dihydrochloride salt as shown below:

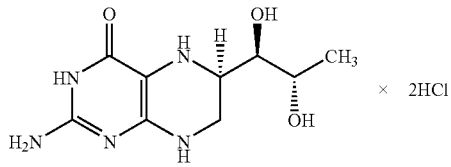

The reduction of a compound of Formula 10 is carried out either according to methods well known in the common literature (e.g., sodium borohydride in a alkaline medium) or preferably with a catalytic amount of platinum dioxide and hydrogen.

Tetrahydrobiopterin may be isolated preferably as dihydrochloride by crystallization techniques well known in the art, such as suspension, precipitation, re-crystallization, evaporation, solvent like water sorption methods or decomposition of solvates. Diluted, saturated, or super-saturated solutions may be used for crystallization, with or without seeding with suitable nucleating agents.

Another embodiment of the processes and compounds described herein is a process for forming enantiomerically-enriched tetrahydrobiopterin or a salt thereof, including the following steps: (a) reacting pterin at the C-6 position to prepare a 6-substituted pterin; (b) protecting the primary amine group at C-2 of neopterin with a 2-amino protecting group; (c) metalation of the protected 6-substituted pterin; (d) coupling of the product of the metalation of the protected 6-substituted pterin with lactic acid or a precursor of lactic acid; (e) removing the 2-amino protecting group; and (f) erythro-selective reduction.

The first step in this embodiment utilizes a 6-substituted pterin, including but not limited to 6-halogenated pterins and 6-sulfonated pterins. Preferably, the 6-substituted pterins are 6-halogenated pterins, more preferably, the pterin starting material is selected from the group consisting of 6-chloropterin, 6-bromopterin, and 6-iodopterin. It has been found that 6-iodopterin is the preferred 6-halogenated pterins for use in the coupling reaction described below.

Figure 3:
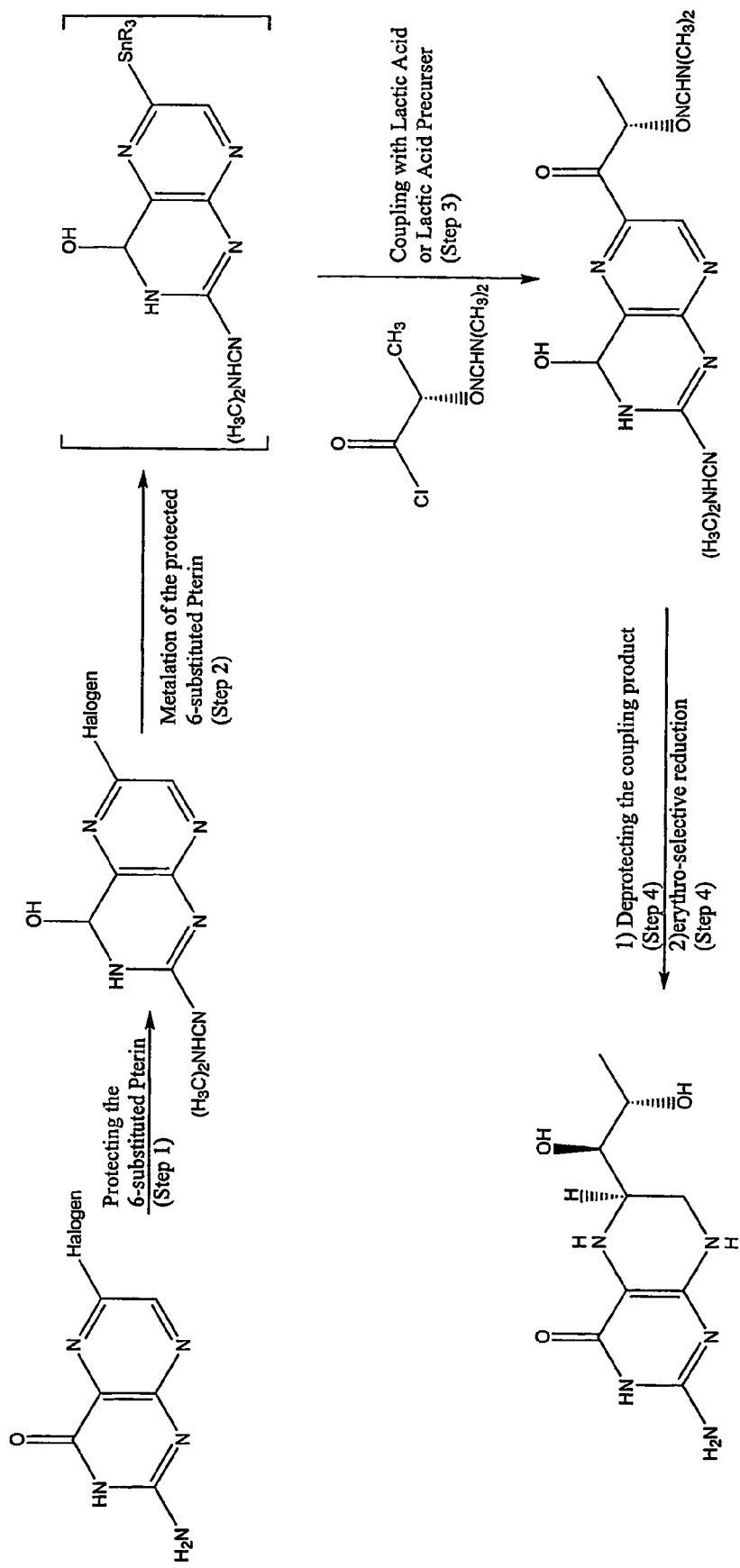
FIG. 3 is a schematic representation of a process described herein for the conversion of a 6-substituted Pterin to Tetrahydrobiopterin.

The first step in this embodiment is the protection the 2-amino group of the 6-substituted pterin, as exemplified in FIG. 3 as Step 1, is the protection of the 2-amino group in the 6-substituted pterin. The protection of the 2-amino group is performed as described above (for the preparation of a compound of Formula 6 (exemplified as Step 4 in FIG. 2), and the product of this step is a compound of Formula 2 (shown below).

Preferably, the protecting group used to protect the 2-amino group is selected from the group consisting of linear chain alkyl single substituted amido groups, branched chain alkyl single substituted amido groups, aryl substituted amido group, a pivaloyl group, and 2,2-dimethylpropanamido. More preferably, the protecting group is a pivaloyl group.

Thus, another embodiment of the processes and compounds described herein is a compound of Formula 2:

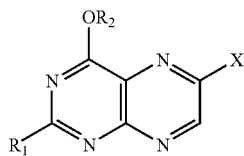

wherein X is selected from the group consisting of chlorine, bromine, iodine, and sulfonates; R1 is selected from the group consisting of single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, branched chain alkyl substituted sulfur groups, single linear chain alkyl substituted alkylaminomethylene-imine groups, single branched chain alkyl substituted alkylaminomethylene-imine groups, double linear chain alkyl substituted alkylaminomethylene-imine groups, and double branched chain alkyl substituted alkylaminomethylene-imine groups; and R2 is selected from the group consisting of hydrogen, linear chain alkyl groups, branched chain alkyl groups, and aryl groups.

The next step in this embodiment of the processes disclosed herein is the metalation of the 6-substituted pterin as exemplified in FIG. 3 as Step 2. Preferably, the metalation of the protected 6-substituted pterin is performed with a reagent selected from the group consisting of RMgX (i.e., a Grignard reagent), alkyl-metal complexes, and metals, wherein X is a halogen, and R is selected from the group consisting of alkyl groups, and aryl groups. Preferably, the alkyl-metal complex is an alkyl-metallic lithium complex, more preferably n-butyllithium and/or t-butyllithium.

The metalation at the 6-position on the pterin produces a pterin derivative, which is not isolated according to this embodiment, but exists for a substantial period of time. Thus, another embodiment of the processes and compounds described herein is a compound of Formula 3:

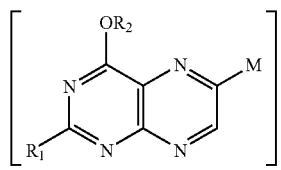

wherein R1 is selected from the group consisting of single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups; branched chain alkyl substituted sulfur groups, and 2,2-dimethylpropanamide; R2 is selected from the group consisting of hydrogen, linear chain alkyl groups, branched chain alkyl groups, and aryl groups; and M is selected from the group consisting of boron, silicon, zirconium, titanium, sodium, aluminum, nickel, cobalt, scandium, chromium, ytterbium, lithium, magnesium, zinc, palladium, copper, manganese, cesium, and tin.

The metalation reaction is preferably performed in non-polar solvents such as ethers, preferably diethylether, dioxane, and/or tetrahydrofuran (THF). Preferably, the metalation is performed with a Grignard reagent, and preferably the Grignard reagent is isopropylmagnesiumchloride. The reaction temperature during the metalation set is preferably kept in the range of about −80° C. up to about +30° C., and preferably one to four equivalents of the metalating reagent (e.g., Grignard reagent) are used for the metalation.

The next step in this embodiment is the coupling of the product from the metalation step with lactic acid or a lactic acid precursor as exemplified in FIG. 3 as Step 3. Preferably, the coupling is performed between the protected 6-metalated pterin and a protected lactic acid chloride, more preferably between the protected 6-metalated pterin and a hydroxyl protected lactic acid chloride such as 2-acetoxypropionic chloride. Preferably, when a precursor of lactic acid is used in this step, the precursor of lactic acid is selected from the group consisting of 2-oxopropanoyl chlorides, and 2-oxopropanal.

It has been found to be preferable that the metalation step and the coupling step can be performed in the same reaction vessel. Accordingly, another embodiment of the processes and compounds described herein is a compound of Formula 3:

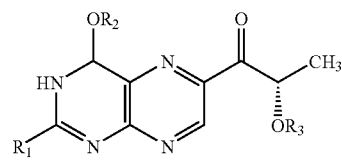

wherein R1 is selected from the group consisting of $NH_2$, 2,2-dimethylpropanamide, single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, and branched chain alkyl substituted sulfur groups; R2 is selected from the group consisting of hydrogen, linear chain alkyl groups, branched chain alkyl groups, and aryl groups; and R3 is an acyl group. Preferably, R1 is an N,N-dimethylaminomethylene substituted amino group.

The coupling step can also be performed with a 2-oxopropanoyl chlorides or with 2-oxopropanale with the use of $Pd(OAc)_2$, $Me_6Sn_2$, $PPh_3$ in dioxane, then $Pd(PPh_3)Cl_2$ and lactic acid chloride or derivatives thereof. A discussion of the reaction conditions and details of processes related to the coupling reaction can be found in Bradshaw et al, J. Chem. Soc., Perkin Trans., 1, 3239-3244 (2001), and Pellicciari et al, Tetrahedron Lett., 3003-3004 (1992), the disclosures of which are hereby incorporated herein by reference. It has also been found preferable that diketones are formed when these reactants are used in the coupling step. Thus, preferably when diketones are formed, the coupling step is followed by the further step of reducing the resulting diketones.

The next step in this embodiment of the processes described herein is deprotecting of the coupling product, and the erythro-selective reduction of the deprotected product to yield tetrahydrobiopterin as exemplified in FIG. 3 as Steps 4 and 5. It has been found that when an acyl group is used as the protecting group R3 in a compound of Formula 4, the protecting group on the can be performed wherein on the protecting group at the 2-amino position is removed. Thus, another embodiment of the processes and compound described herein is a compound of Formula 5:

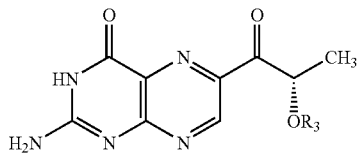

wherein R3 is an acyl group.

The tetrahydrobiopterin prepared by the reduction, as exemplified in FIG. 3 as Step 5, can then be converted to its salt form, including but not limited to its dihydrochloride salt as shown below:

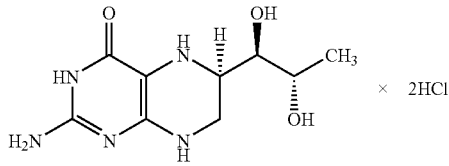

The erythro-selective reduction of a compound of Formula 4 is carried out either according to methods well known in the common literature (e.g. sodium borohydride in a alkaline medium) or preferably with a catalytic amount of platinum dioxide and hydrogen.

Tetrahydrobiopterin may be isolated preferably as dihydrochloride by crystallization techniques well known in the art, such as suspension, precipitation, re-crystallization, evaporation, solvent like water sorption methods or decomposition of solvates. Diluted, saturated, or super-saturated solutions may be used for crystallization, with or without seeding with suitable nucleating agents.

It has been found that the primary hydroxyl of neopterin can be reduced, and leave a methyl group at the C-3' position of the neopterin. This conversion is performed by converting the primary hydroxyl to a thioether, and then reduction of the thioether to a methyl group. Thus, another embodiment of the processes and compounds described herein is a process for forming enantiomerically-enriched tetrahydrobiopterin or a salt thereof from neopterin, including the following steps: (a) protecting the primary amine group at C-2 of neopterin with a 2-amino protecting group; (b) converting the primary hydroxyl group of neopterin to a thioether; and (c) reduction of the thioether leaving a methyl group at the C-3' position on the neopterin side chain.

Quite surprisingly, it has been found that when step (c) above is performed at elevated temperatures (e.g., above 50 degrees Celsius), the reaction conditions for the reduction reaction of step (c) will also remove the 2-amino protecting group and perform an erythro-selective reduction of the C5-C6 and C7-C8 double bonds on neopterin to yield tetrahydrobiopterin. Thus, it is preferred to perform the reduction reaction of step (c) at elevated temperatures and allow the reaction to be preformed under an excess of reducing agent to allow the removal of the 2-amino protecting group and an erythro-selective reduction.

As described below, if the reduction of step (c) does not result in the erythro-selective reduction of the C5-C6 and C7-C8 and the removal of the 2-amino protecting group, the process further includes the two additional steps of removal of the 2-amino protecting group and an erythro-selective hydrogenation.

It has been found that the purity and stability of the tetrahydrobiopterin product produced according to this embodiment can be improved by forming a salt of tetrahydrobiopterin. Thus, the tetrahydrobiopterin is preferably conferred to its corresponding salt, more preferable to the dichloride salt of tetrahydrobiopterin. Preferably, the dichloride salt of tetrahydrobiopterin is further recrystallized.

Figure 4:
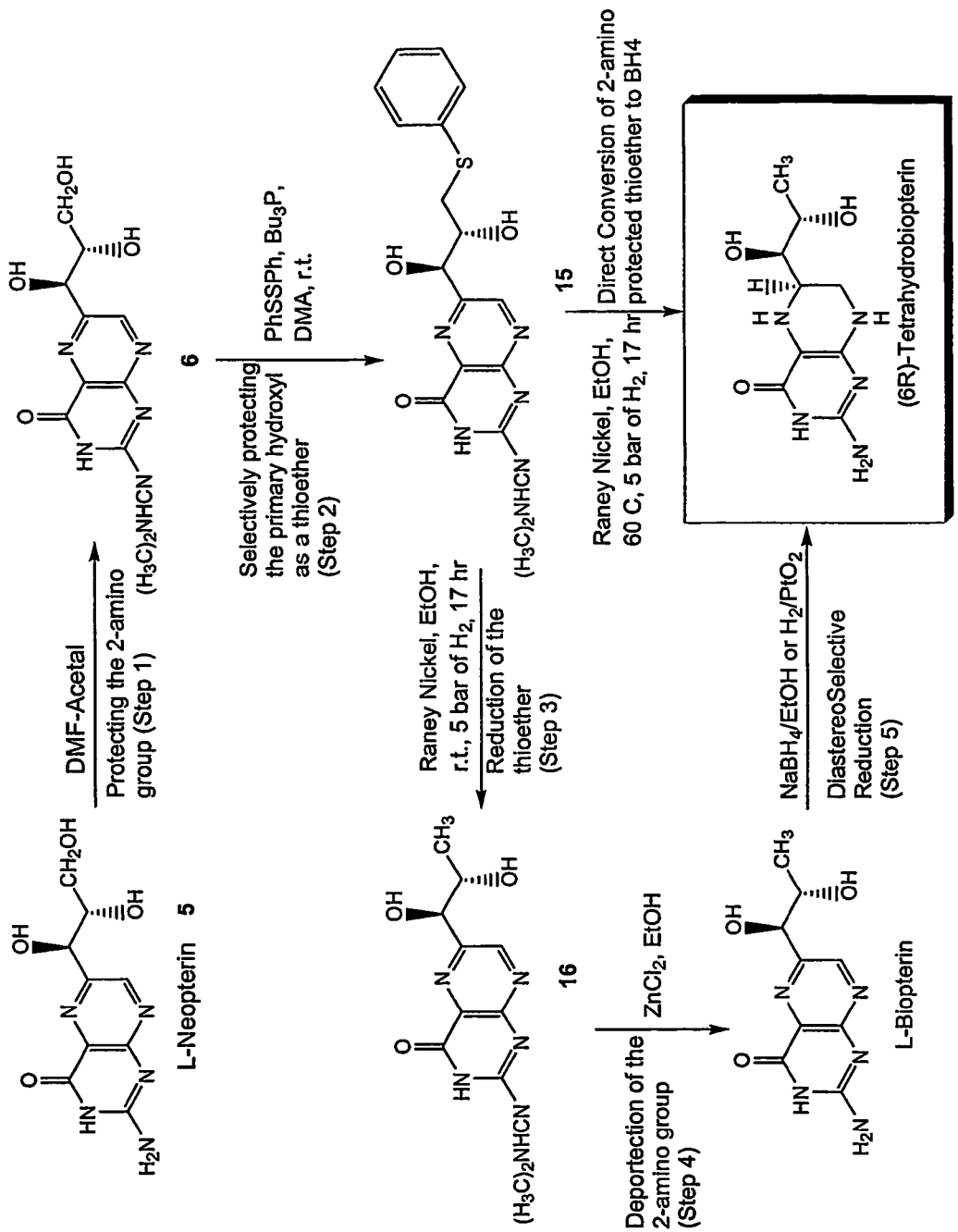
FIG. 4 is a is a schematic representation of a process described herein for the conversion of L-Neopterin to Tetrahydrobiopterin, wherein the primary hydroxyl group on L-Neopterin is converted to its corresponding thioether, and the resulting thioether is then reduced to product a deoxygenated Neopterin derivative.

The first step in this embodiment, as exemplified in FIG. 4 as Step 1, is the protection of the 2-amino group on L-Neopterin. The protection of the 2-amino group on the L-Neopterin is preferably performing using a variety of protecting groups. Preferably, the protecting group for the 2-amino position on L-Neopterin is selected from the group consisting of dialkylformamidedialkylacetal groups, and pivaloyl groups. More preferably, the protecting group is one of N,N-dimethylformamidediethylacetal, and N,N-dimethylformamidedimethylacetal.

Protecting the 2-amino group dialkylformamidedialkylacetals yields the selective protection of the 2-amino group, and is described in Brederick et al, Chem. Ber., 101 41-50, (1968), and generally in Russel et al., Synlett 1992, p. 711, the disclosures of which are hereby incorporated herein by reference. Preferably, the reaction to protect the 2-amino group is carried out in a polar solvent, more preferably in dimethylformamide. In addition the 2-(N,N-dialkylaminomethyleneimino) Neopterin derivatives are much more soluble in non-polar organic solvents than the unprotected neopterin, and the protection of the 2-amino group to with a 2-(N,N-dialkylaminomethylene-imino) protecting group could be performed in a less polar solvent than DMF.

The second step in this embodiment, as exemplified in FIG. 2 as Step 2, is the conversion of the primary hydroxyl group to a thioether. This conversion is preferably performed with the use of the Hata reagent. Thus, the primary hydroxyl is selectively converted to a thioether with the use of a disulfide reagent and a trialkylphosphine reagent, more preferably diphenyl disulfide and tributylphosphine.

Another embodiment of the processes and compounds disclosed herein is a compound of Formula 15:

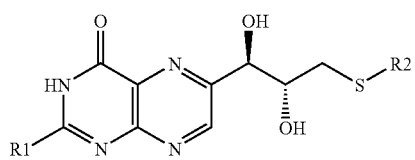

wherein R1 is selected from the group consisting of single linear chain alkyl substituted amino groups, single branched chain alkyl substituted amino groups, double linear chain alkyl substituted amino groups, double branched chain alkyl substituted amino groups, aryl single substituted amino groups, linear chain alkyl substituted sulfur groups, branched chain alkyl substituted sulfur groups, single linear chain alkyl substituted alkylaminomethyleneimine groups, or single branched chain alkyl substituted alkylaminomethyleneimine groups, double linear chain alkyl substituted alkylaminomethyleneimine groups, double branched chain alkyl substituted alkylaminomethyleneimine groups; and R2 is selected from the group consisting of linear chain alkyl groups, branched chain alkyl groups, and aryl groups. Preferably, R1 is a dialkylalkylaminomethyleneimine group, more preferably, dimethylaminomethyleneimine. Also preferably, R2 is benzene.

The next step in the process of this embodiment, as exemplified in FIG. 4 as Step 3, is the reduction of the thioether, wherein the net result is the replacement of the thioether with a hydrogen (i.e., 2-amino protected Biopterin). Preferably, the reduction of the thioether is performed with the use of a Raney-Nickel a reducing agent. It has been found that the reduction of the thioether does not proceed to yield product (i.e., 2-amino protected L-Biopterin) when the reaction is carried out in a protic solvent. Thus, the reduction reaction is preferably performed in a polar aprotic solvent and at room temperature.

As described above, when the reduction of the thioether is performed at room temperature and carefully monitored, the reduction does not result in a removal of the 2-amino protecting group and an erythro-selective reduction. Accordingly, the next two steps in this embodiment, as exemplified in FIG. 4 as Steps 4 and 5, include the deprotection of the 2-amino group (i.e., removal of the 2-amino protecting group), and the erythro-selective reduction of the product resulting from the deprotection (i.e., L-Biopterin). The specific reaction conditions for the deprotection and reduction steps are described above, and in the references listed above.

EXAMPLES

The following examples are provided to illustrate the processes and compounds described herein but are not intended to limit the scope of the processes and compounds described herein.

Example 1

The preparation of a N2-N,N-Dimethylaminomethylene-L-neopterin (a compound of Formula 6 wherein R1 is an dimethylaminomethylene-imine group) was prepared by adding 15.8 ml of N,N-dimethylformamidediethylacetal to a flask containing a suspension of 11.68 g of L-neopterin and 850 ml of dry N,N-dimethylformamide. The mixture was stirred at room temperature until all starting material dissolved. After 6 hours of stirring at room temperature, 280 ml dry methanol was added and the reaction mixture and the mixture was stirred for an additional 12 hours. After evaporating all solvents the residue from the reaction mixture was suspended in 500 ml of dichloromethane, the suspended material was then collected and washed with 150 ml of dichloromethane, and the resulting product was vacuum dried at 40° C. to give 11.23 g of N2-N,N-dimethylaminomethylene-L-neopterin.

The 1H-NMR-data (200 MHz, solvent: DMSO-d6) for the protected L Neopterin is as follows: 11.98 ppm, bs, N3-H; 1H, 8.79 ppm, s, CH=N, C7-H, 2H, 5.64 ppm, d, C1'-OH, 1H, 4.75 ppm, d, C2'-OH, 1H, 4.63 ppm, dd, C1'-H, 1H; 4.47 ppm, t, C3'-OH, 1H, 3.81 ppm, m, C2'H, 1H, 3.54 ppm, m, C3'H1, 1H, 3.43 ppm, m, C3'H2, 1H, 3.22 ppm, s, N—CH3, 3H, 3.09 ppm, s, N—CH3, 3H.

Example 2

The selective protection of the primary hydroxyl group was performed with the 2-amino protected L-Neopterin that was prepared according to Example 1. The N2-N,N-Dimethylaminomethylene-3'O(t-butyl-diphenylsilyl)-L-neopterin was prepared by first suspending 10 g of N2-N,N-Dimethylaminomethylen-L-neopterin in 250 ml of dry N,N-dimethylformamide, and then adding 4.9 g imidazole and 10 g t-butyldiphenylchlorosilane to the reaction mixture. After the reaction mixture stirred at room temperature for 2 hours an additional 0.5 g imidazole and 1 g t-butyldiphenylchlorosilan. After the reaction mixture stirred for an additional 14 hours at room temperature the reaction mixture was evaporated to dryness and the residue was purified by flash chromatography on silica gel using a gradient of dichloromethane/methanol of 9:1 to 6:4. Product fractions were pooled and evaporated. The residue was suspended in 100 ml of isopropanol and the product was collected, washed with isopropanol, and vacuum dried at 40° C. to give 9.3 g of N2-N,N-Dimethylaminomethylen-3'(t-butyl-diphenylsilyl)-L-neopterin.

The 1H-NMR-data (200 MHz, solvent: DMSO-d6) for the product is as follows: 11.99 ppm, bs, N3-H; 1H, 8.82 ppm, s, CH=N, C7-H, 2H, 7.63 ppm, m, Ph, 4H, 7.41 ppm, m, Ph, 6H; 5.73 ppm, d, C1'-OH, 1H, 5.00 ppm, d, C2'-OH, 1H, 4.79 ppm, dd, C1'-H, 1H, 4.05 ppm, m, C2H, 1H, 3.78 ppm, m, C3'H1, 1H, 3.68 ppm, m, C3'H2, 1H, 3.23 ppm, s, N—CH3, 3H, 3.10 ppm, s, N—CH3, 3H, 0.93 ppm, s, C(CH3)3, 9H.

Example 3

The selective protection of the primary hydroxyl group was also performed with the 2-amino protected L-Neopterin that was prepared according to Example 1, and after the selective protection, the deprotection of the 2-amino group was performed in the same reaction flask to yield 3'O-(t-butyl-diphenylsilyl)-L-neopterin.

To a suspension of 8 g of N2-N,N-Dimethylaminomethylen-L-neopterin in 200 ml of dry N,N-dimethylformamide were added 3.92 g imidazole and 8 g t-butyldiphenylchlorosilane. After the reaction mixture stirred for 2 hours at room temperature, an additional 0.4 g of imidazole and 0.8 g of t-butyldiphenylchlorosilane was added. The reaction mixture was then allowed to stir at room temperature for 14 hours after which the reaction mixture was evaporated to dryness and the residue of crude N2-N,N-Dimethylaminomethylen-3'(t-butyl-diphenylsilyl)-L-neopterin was dissolved in 160 ml ethanol. Upon dissolution in ethanol, 15 g of zinc-chloride was added to the reaction flask, and the mixture was heated to 80° C. for 3 hours. During the course of the three hours a solid separated out from the mixture. The suspension was then cooled to 58° C. and the solid was collected, washed with 100 ml ethanol and dried in vacuum at 40° C. to give 5 g of 3'(t-butyl-diphenylsilyl)-L-neopterin. Another 5 g fraction of 3'(t-butyl-diphenylsilyl)-L-neopterin was obtained from the filtrate after leaving it at room temperature for 24 hours.

The 1H-NMR-data (200 MHz, solvent: DMSO-d6) for 3'O-(t-butyl-diphenylsilyl)-L-neopterin was as follows: 11.40 ppm, bs, N3-H; 1H, 8.73 ppm, s, CH=N, C7-H, 2H, 7.63 ppm, m, Ph, 4H, 7.42 ppm, m, Ph, 6H, 6.86 ppm, bs, NH2, 2H, 5.68 ppm, d, C1'-OH, 1H, 4.97 ppm, d, C2'-OH, 1H, 4.74 ppm, dd, C1'-H, 1H, 4.02 ppm, m, C2H, 1H, 3.77 ppm, m, C3'H1, 1H, 3.66 ppm, m, C3'H2, 1H, 0.93 ppm, s, C(CH3)3, 9H.

Example 4

The protection of the secondary hydroxyl groups was performed to prepare 1'2'-isopropylidene-3'O-(t-butyl-diphenylsilyl)-L-neopterin by adding 3.8 g para-toluenesulfonic acid to a reaction flask containing 10 g 3'(t-butyl-diphenylsilyl)-L-neopterin (prepared according to Example 3) in 50 ml acetone-dimethylacetal. The reaction mixture was allowed to stir for 14 hours at room temperature. The resulting solid was collected, washed with 30 ml of acetone-dimethylacetal and vacuum dried at 35° C. to yield 6.5 g of 1'2'-isopropylidene-3'(t-butyl-diphenylsilyl)-L-neopterin.

The foregoing description is given for clearness of understanding only, and no unnecessary limitations should be understood therefrom, as modifications within the scope of the processes and compounds described herein may be apparent to those having ordinary skill in the art.

Example 5

The conversion of the primary hydroxyl of L-Neopterin to a thioether was performed to prepare 6-((1R,2R)-1,2-dihydroxy-3-phenylthiopropyl)-2-[(methylethyl)amino]-3-hydropteridin-4-one (the compound labeled "15" in FIG. 4). To a flask containing 50 grams of 6-((2S,1R)-1,2,3-trihydroxypropyl)-2-[(1Z)-1-aza-2-(dimethylamino)vinyl]-3-hydropteridin-4-one (DMA-Neopterin, the compound labeled "6" in FIG. 2) and 400 ml of dimethylaminoacetate was added to the flask. To this stirring mixture 1 molar equivalent of diphenyl disulfide and tributylphosphine were added to the flask. It was discovered that the DMA-Neopterin has a low solubility in dimethylaminoacetate at room temperature (approximately 3.5 mg/ml). It is believed that the thioether product is more soluble in dimethylaminoacetate. The reaction mixture was allowed to was allowed to stir for 4 hours at room temperature. Nine grams of the thioether product was isolated.

Example 6

The thioether product prepared in Example 5 was reduced with Raney-Nickel according to the following procedure. The thioether (9 grams, 22 mmole) was added to a flask, and the flask was charged with 360 ml of ethanol. To a stirring mixture of the thioether in ethanol, 90 grams of Raney-Nickel in ethanol, and the reaction mixture was placed under an atmosphere of hydrogen of 5 bar of pressure. The reaction mixture was allowed to stir for 17 hours.

The hydrogen pressure was then released, the Raney-Nickel was filtered off from the reaction mixture, and 2.25 ml of concentrated hydrochloric acid was added to the filtrate. The resulting dihydrochloride salts were then collected and separated. Two diastereomers of BH4 dihydrochloride salt was formed in the reaction, the desired (6R) form was prepared in 15.8 percent yield, and the undesired (6S) form was prepared in 9.3% yield.

The foregoing description is given for clearness of understanding only, and no unnecessary limitations should be understood therefrom, as modifications within the scope of the processes and compounds described herein may be apparent to those having ordinary skill in the art.

What is claimed is:

1. A process for forming enantiomerically-enriched tetrahydrobiopterin (BH4) or a salt thereof from neopterin, comprising the steps of:
   (a) protecting the primary amine group at C-2 of neopterin with an amino protecting group;
   (b) converting the primary hydroxyl group of neopterin to a thioether; and
   (c) reducing the thioether of step (b) to a methyl group.

2. The process of claim 1, wherein step (c) also results in removal of the primary amine protecting group and erythro-selective reduction to form BH4 or a salt thereof.

3. The process of claim 1, wherein the erythro-selective reduction comprises using Raney nickel and hydrogen.

4. The process of claim 1, further comprising the step of removing the primary amine protecting group after step (c).

5. The process of claim 4, wherein the removing comprises reacting with zinc dichloride in ethanol.

6. The process of claim 4, further comprising the step of performing an erythro-selective reduction to form BH4 or a salt thereof.

7. The process of claim 6, wherein the erythro-selective reduction comprises using (1) sodium borohydride in an alkaline medium or (2) hydrogen and a catalytic amount of platinum dioxide.

* * * * *